United States Patent [19]

Siclari et al.

[11] 4,218,399

[45] Aug. 19, 1980

[54] METHOD FOR PREPARING α, ω-DIAMINES

[75] Inventors: Francesco Siclari, Barlassina; Pietro P. Rossi, Garlasco; Mario De Gaetano, Cesano Maderno, all of Italy

[73] Assignee: SNIA VISDOSA Società Nazionale Industria Applicazioni Viscosa S.p.A., Milan, Italy

[21] Appl. No.: 14,633

[22] Filed: Feb. 23, 1979

[30] Foreign Application Priority Data

Feb. 28, 1978 [IT] Italy .................................. 20679 A/78

[51] Int. Cl.$^2$ ........................ C07C 85/08; C07C 85/24
[52] U.S. Cl. ............................ 260/583 P; 260/583 H; 260/584 R; 260/585 C
[58] Field of Search ............ 260/585 C, 583 H, 583 P, 260/584 R

[56] References Cited

U.S. PATENT DOCUMENTS

| 1,966,478 | 7/1934 | Baur ................................. 260/585 C |
| 2,636,051 | 4/1953 | Whetstone et al. .............. 260/584 R |
| 3,412,156 | 11/1968 | Ueda et al. ....................... 260/583 P |

OTHER PUBLICATIONS

Augustine, "Catalytic Hydrogenation", pp. 57, 102 & 103, (1965).

*Primary Examiner*—John Doll
*Attorney, Agent, or Firm*—Wenderoth, Lind & Ponack

[57] ABSTRACT

A method is disclosed for preparing α, ω-diamines by reductive amination of corresponding α, ω-dialdehydes with ammonia in an aqueous mixture of butyl alcohol.

5 Claims, No Drawings

METHOD FOR PREPARING α, ω-DIAMINES

BACKGROUND OF THE INVENTION

A method has been developed by the Applicants for preparing straight chain saturated or unsaturated aliphatic α, ω -diamines containing from 8 to 12 carbon atoms, by reductive amination of the corresponding α, ω -dialdehydes.

More particularly, the subject matter of the study by the Applicants is characterized in that the α, ω -dialdehyde is first converted into the corresponding diimine by low temperature reaction in an aqueous mixture of an organic solvent with ammonia, and that the diimine thus obtained is then subjected to reaction with hydrogen in the presence of a catalyst which, under the reaction conditions, is effective to reduce all the double imino bonds, while leaving the olefin bonds, if any, unaltered, and in the event of olefin bonds being present and a saturated α, ω -diamine being the desired product, the resulting unsaturated diamine is subjected to hydrogenation in the presence of a catalyst selected from palladium, platinum, ruthenium, and rhodium.

Thus, in accordance with that study, starting from unsaturated dialdehydes, there can be obtained both the corresponding unsaturated diamines and the saturated ones, while from the saturated dialdehydes the corresponding saturated diamines are obtained.

For use as an organic solvent in the aqueous mixture, wherein the α, ω -dialdehyde is reacted with ammonia, an alcohol is indicated, preferably ethyl alcohol, dioxane, or tetrahydrofuran.

SUMMARY OF THE INVENTION

Now, it was found, and this forms the subject matter of this invention, that surprisingly, when butyl alcohol is used as the organic solvent, an appreciable increase is achieved in the yield of the final product.

The reaction of the α, ω -dialdehyde with the ammonia is carried out at a temperature in the range of from −50° C. to −5° C., preferably from −35° C. to −10° C., and at a pressure not necessarily above atmospheric pressure.

The subsequent hydrogenation of the resulting diimines is preferably carried out under the same conditions as indicated by the cited Applicant's study. Obviously, here also, butyl alcohol is preferably employed as the suitable solvent.

DESCRIPTION OF THE PREFERRED EMBODIMENTS

The method according to this invention is preferably carried out in conformity with the following conditions:

(a) the reaction of the α, ω -dialdehyde with ammonia is carried out at a temperature in the range of from −35° C. to −10° C.;

(b) the α, ω -dialdehyde is introduced, preferably in the form of a butanol solution, in the ammonia solution;

(c) the molar ratio of ammonia to the —CHO groups is maintained > than 5:1;

(d) the solution of the diimine resulting from the reaction of ammonia with the dialdehyde is passed to the hydrogenation autoclave, wherein there is already established a pressure of 15 to 80 atm and a temperature of 60° C. to 150° C.;

(e) the hydrogenation catalyst is, at the time of adding the diimine, already suspended in the aqueous butyl alcohol within the autoclave, at a temperature of from 60° C. to 150° C.

As the hydrogenation catalyst, finely divided nickel is preferred, as obtained by decomposition of nickel formate in cyclododecane at 230°-240° C.

According to an even more preferred embodiment of the inventive method, the hydrogenation reaction is continued for a period ranging from 5 to 60 minutes.

The resulting α, ω -diamine is then isolated and purified by known methods.

If saturated α, ω -diamine is the product to be obtained, starting from an unsaturated α, ω -dialdehyde, then the unsaturated α, ω -diamine, as prepared by hydrogenation with Ni or Co, is subsequently subjected to further hydrogenation in the presence of a catalyst selected from palladium, ruthenium, rhodium, and platinum, said hydrogenation step being carried out in a conventional manner in the presence among others, of butyl alcohol, such as a mixture of butyl alcohol-water wherein the catalyst is suspended, under a pressure of from 5 to about 80 atm and a temperature of from 60° C. to 150° C.

The saturated diamine thus obtained is then isolated and purified in accordance with known methods.

The following example is illustrative but not limitative.

EXAMPLE 86.4 g (0.43 moles) of a 98,5% 1,12-dodecadiene-4,8-diale (as prepared by reduction, at −5° C. with zinc and water, of an alcoholic-acetic solution of the cyclododecatriene ozonide obtained in acetic acid and cyclohexane) are admixed with 86 g. of n-butyl alcohol and added dropwise to a butanol solution composed of 9.0 moles of $NH_3$, 30 g. of water, and 370 g. of n-butanol, maintained at a temperature of −10° C. The solution thus obtained is introduced by means of a metering pump and an inlet feed pipe maintained at −10° C. into an autoclave containing 15 g. of finely divided nickel (prepared for example by decomposition of nickel formate in boiling cyclododecane), 6 moles of ammonia, 50 g. of water and 160 g. of n-butanol, the temperature of said mixture being of 130° C. and the total hydrogen and ammonia pressure in the autoclave being at 40 atm.

At the end of the addition of the solution, the reaction is continued under a pressure of 40 atm. for additional 10 minutes at 135° C.

At the end of this period, the autoclave is suitably cooled, the pressure is discharged, the catalyst is separated by filtration and the reaction product is subjected to vacuum distillation.

There are thus obtained 79.0 g. of 1,12-dodecadienediamine (1,12-diamine dodeca-4,8-diene) having a boiling point at 0.3 mm Hg of 128°-130° C., corresponding to a yield of 92%.

Operating under the same conditions except for using ethyl alcohol in place of butyl alcohol, a yield of only 78% results.

Operating according to the preceding example except for subjecting to reductive amination a dialdehyde having from 8 to 10 carbon atoms, there is achieved, by using butyl alcohol instead of ethyl alcohol, a corresponding increase of the yield, similarly to that indicated in the preceding example.

I claim:

1. A method for preparing straight chain saturated or unsaturated aliphatic α, ω -diamines containing from 8 to 12 carbon atoms, by reductive amination of the corresponding $\alpha, \omega$-dialdehydes, comprising firstly converting a said $\alpha, \omega$-dialdehyde to di-imine by reaction with ammonia and then hydrogenating the so-obtained di-imine, the method being characterized in that the reaction of dialdehyde with ammonia is carried out in an aqueous mixture of butyl alcohol.

2. A method according to claim 1, characterized in that the reaction of dialdehyde with ammonia is carried out at a temperature from $-50°$ C. to $-5°$ C., preferably from $-35°$ C. to $-10°$ C., the alcoholic dialdehyde being added to the ammonia solution.

3. A method according to claim 1, characterized in that the diimine is passed, for hydrogenation, to an autoclave containing the hydrogenation catalyst in the form of a suspension in butyl alcohol.

4. A method according to claim 1, characterized in that the reduction of the diimine is carried out under a pressure in the range from 15 to 80 atm, at a temperature in the range from $60°$ C. to $150°$ C., and in the presence of a finely divided nickel catalyst.

5. A method according to claim 1, for producing a saturated diamine from an unsaturated dialdehyde, characterized in that it further comprises hydrogenating the unsaturated diamine obtained from the reductive amination of the unsaturated dialdehyde in a butyl alcohol solution and in the presence of a catalyst selected from palladium, ruthenium, rhodium, and platinum, under a pressure in the range from 5 to 80 atm, at a temperature in the range from $60°$ C. to $150°$ C.

* * * * *

UNITED STATES PATENT AND TRADEMARK OFFICE
CERTIFICATE OF CORRECTION

PATENT NO. : 4,218,399
DATED : August 19, 1980
INVENTOR(S) : Francesco Siclari, Pietro P. Rossi, Mario De Gaetano It is certified that error appears in the above-identified patent and that said Letters Patent are hereby corrected as shown below:

First Cover Page, Col. 1, line [73]

Change "VISDOSA" to -- VISCOSA -- .

Signed and Sealed this

Fourteenth Day of April 1981

[SEAL]

Attest:

RENE D. TEGTMEYER

Attesting Officer        Acting Commissioner of Patents and Trademarks